(12) United States Patent
Geurts et al.

(10) Patent No.: US 6,700,982 B1
(45) Date of Patent: Mar. 2, 2004

(54) HEARING INSTRUMENT WITH ONSET EMPHASIS

(75) Inventors: Luc J. R. Geurts, Herk-de-Stad (BE); Jan G. M.-T. Wouters, Holsbeek (BE); Stephanus Peeters, Aartselaar (BE)

(73) Assignee: Cochlear Limited, Lane Cove (AU)

( * ) Notice: Subject to any disclaimer, the term of this patent is extended or adjusted under 35 U.S.C. 154(b) by 0 days.

(21) Appl. No.: 09/326,893

(22) Filed: Jun. 7, 1999

(30) Foreign Application Priority Data

Jun. 8, 1998 (EP) .......................................... 98201877

(51) Int. Cl.⁷ ............................................. H04R 25/00
(52) U.S. Cl. ...................................... 381/312; 381/320
(58) Field of Search ............................. 381/312, 320, 381/321, 57, 104, 102; 607/137, 61, 66, 68, 55–57, 62; 600/559, 586; 704/233

(56) References Cited

U.S. PATENT DOCUMENTS

| | | | |
|---|---|---|---|
| 4,061,875 A | * 12/1977 | Freifeld et al. | |
| 4,191,864 A | * 3/1980 | Sopher | |
| 4,249,042 A | * 2/1981 | Orban | |
| 4,357,497 A | * 11/1982 | Hochmair | |
| 4,390,756 A | * 6/1983 | Hoffmann et al. | 607/56 |
| 4,441,202 A | * 4/1984 | Tong et al. | 381/326 |
| 4,515,158 A | * 5/1985 | Patrick et al. | 607/57 |
| 4,536,844 A | 8/1985 | Lyon | 364/487 |
| 4,593,696 A | * 6/1986 | Hochmair et al. | 381/320 |
| 4,887,299 A | * 12/1989 | Cummins et al. | |
| 4,996,712 A | * 2/1991 | Laurence et al. | |
| 5,165,017 A | * 11/1992 | Eddington et al. | |
| 5,215,085 A | 6/1993 | von Wallenberg-Pachaly | 128/420.6 |
| 5,278,912 A | * 1/1994 | Waldhauer | |
| 5,371,803 A | * 12/1994 | Williamson, III | |
| 5,402,498 A | * 3/1995 | Waller, Jr. | |
| 5,488,668 A | * 1/1996 | Waldhauer | |
| 5,903,655 A | * 5/1999 | Salmi et al. | |
| 5,991,663 A | * 11/1999 | Irlicht et al. | 607/56 |
| 6,064,913 A | * 5/2000 | Irlicht et al. | 607/57 |
| 6,078,838 A | * 6/2000 | Rubinstein | 607/55 |
| 6,104,822 A | * 8/2000 | Melanson et al. | |

* cited by examiner

*Primary Examiner*—Curtis Kuntz
*Assistant Examiner*—P. Dabney
(74) *Attorney, Agent, or Firm*—Gottlieb, Rackman & Reisman, P.C.

(57) ABSTRACT

The hearing instrument comprises a circuit (12) for transforming an audio signal (11) into an output signal (13). This circuit (12) comprises emphasis means for emphasising in the output signal (13) substantial intensity changes of the audio signal (11). The emphasis means are embodied so as to emphasise the output signal (13) during a period of about 10 ms when an intensity change rate of the audio signal (11) exceeds a predetermined value. In this way, the time domain response of a normal hearing person is approximated.

14 Claims, 3 Drawing Sheets

HEARING INSTRUMENT WITH ONSET EMPHASIS

BACKGROUND OF THE INVENTION

1. Field of the Invention

Figure 1:
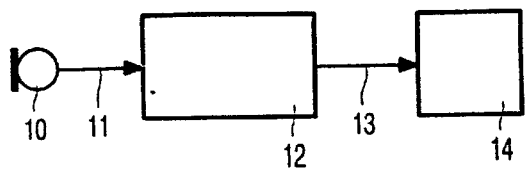

The invention relates to a hearing instrument comprising a circuit for transforming an audio signal into an output signal.

The invention further relates to a circuit for transforming an audio signal into an output signal and a method for transforming an audio signal into an output signal.

2. Description of Related Art

A hearing instrument according to the preamble is known from WO 96/12383. Hearing instruments are used to improve the perception of sounds by hearing impaired persons. In general, such hearing instruments try to transform a received audio signal into a stimulation signal in such a way that by stimulating a persons hearing system with that stimulation signal the hearing of a normal hearing person is approximated as closely as possible.

In the known hearing instrument the transformation of the received audio signal into the stimulation signal comprises the following steps: first, the audio signal is analysed in order to identify the presence of predefined portions, e.g. phonemes, tones or chords, therein. Next, on the basis of the identified portions the stimulation signal is determined, e.g. by using look up tables or by mere calculation, in such a way that the time domain response of a normal hearing person to those portions is approximated.

The transformation of the received audio signal in the known hearing instrument is relatively complex.

BRIEF SUMMARY OF THE INVENTION

An object of the invention is to provide a hearing instrument, wherein the transformation of the received audio signal into the stimulation signal is performed in a relatively simple manner. This object is achieved in the hearing instrument according to the invention, which is characterized in that the circuit comprises emphasis means for emphasising in the output signal substantial intensity changes of the audio signal. The invention is based upon the recognition that the neural activity in a persons hearing system at the onset of a sound stimulus is much higher than the neural activity after the onset. The more suddenly the intensity of the stimulus increases, the higher this activity will be. The duration of this so called short term adaptation is in the order of magnitude of 10 ms. It is assumed that the origin of the adaptation effect is at the inner hair-cell/auditory-nerve synapse. For persons whose hearing system is damaged in such a way that this adaptation effect is not fully present the hearing instrument according to the invention provides an improved perception of sounds. Experiments have shown that, as this hearing instrument emphasises the onset of the typical intensity increases of speech, the speech intelligibility for users can be improved considerably.

An embodiment of the hearing instrument according to the invention is characterized in that the circuit further comprises filter means for filtering the audio signal, whereby the filter means are coupled to the emphasis means so that substantial intensity changes of the filtered audio signal are emphasised in the output signal. In order to approximate a persons hearing system, it can be advantageous to split the frequency spectrum of the received audio signal into several frequency bands or channels. For instance, if the hearing instrument comprises a cochlear implant this can be used to simulate the tonotopic organisation of the cochlea.

A further embodiment of the hearing instrument according to the invention is characterized in that the emphasis means comprise a peak generator for generating from the audio signal a peak signal and including means for including the peak signal in the output signal. By this measure sudden changes in the intensity of the audio signal are transformed into peak signals which are included in the output signal. The duration of these peak signals is preferably in the order of magnitude of 10 ms. The inclusion of the peak signals in the output signal emphasises the onset of substantial intensity changes in the audio signal.

BRIEF DESCRIPTION OF THE INVENTION

Figure 2:
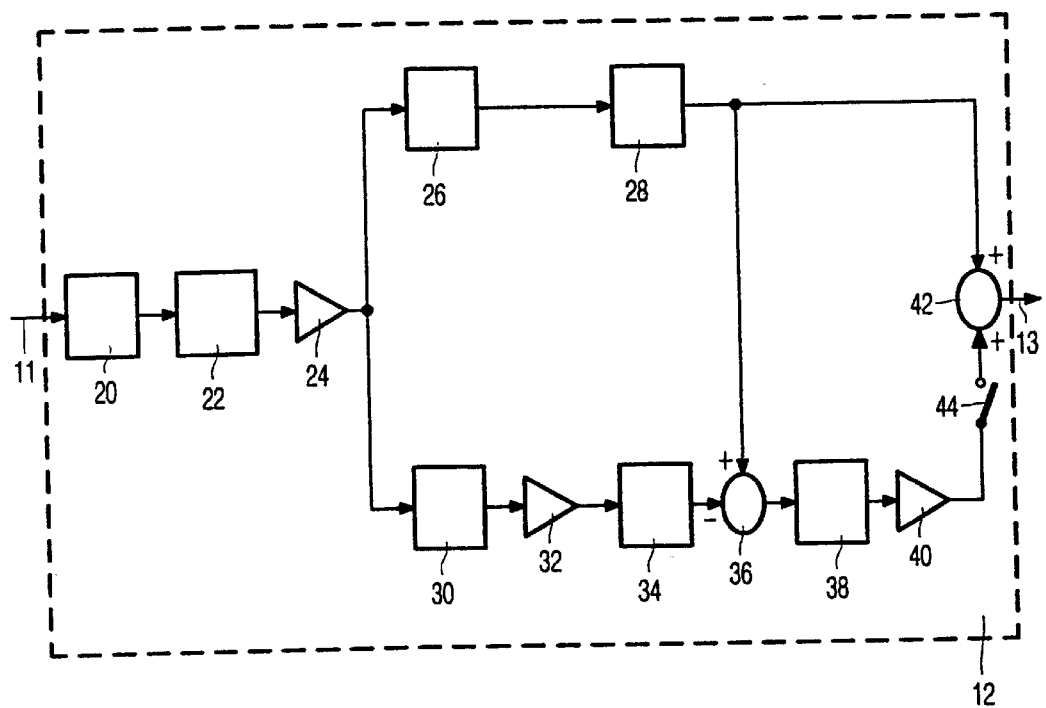
Figure 3:
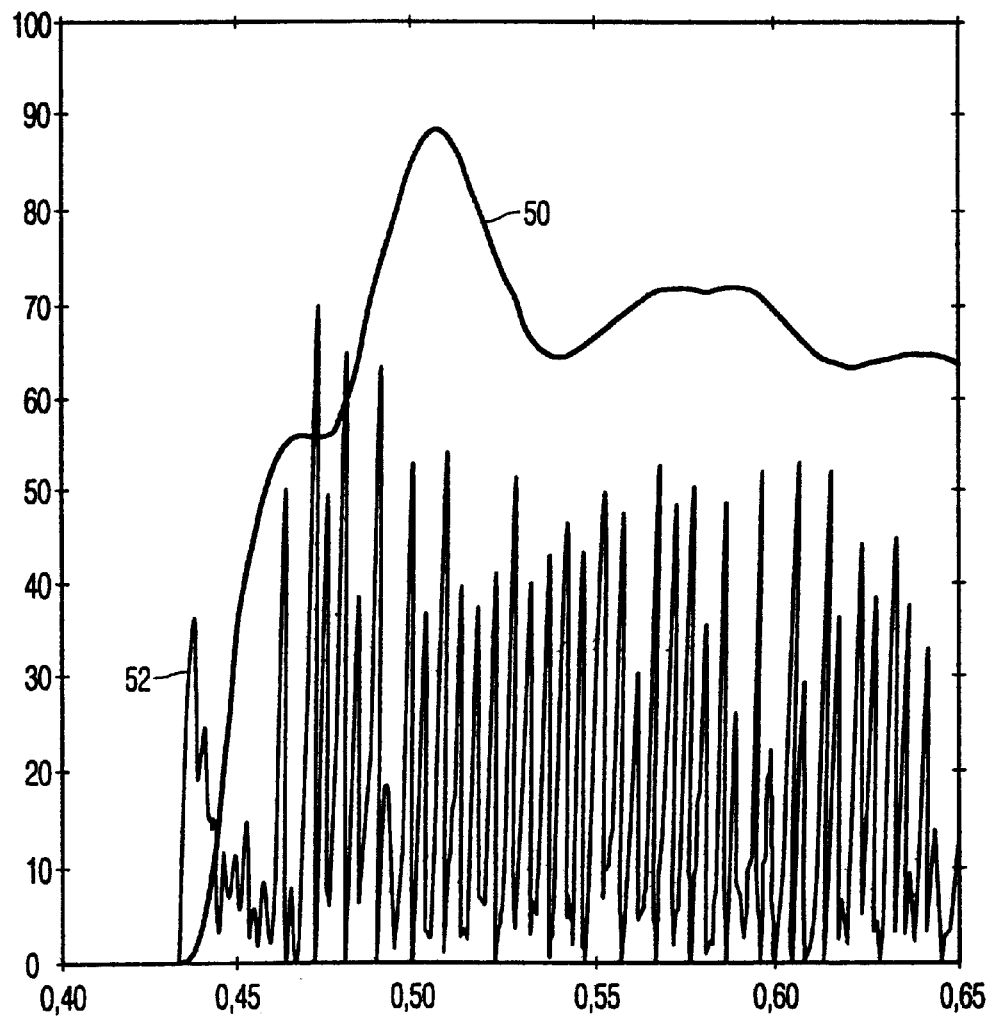
Figure 4:
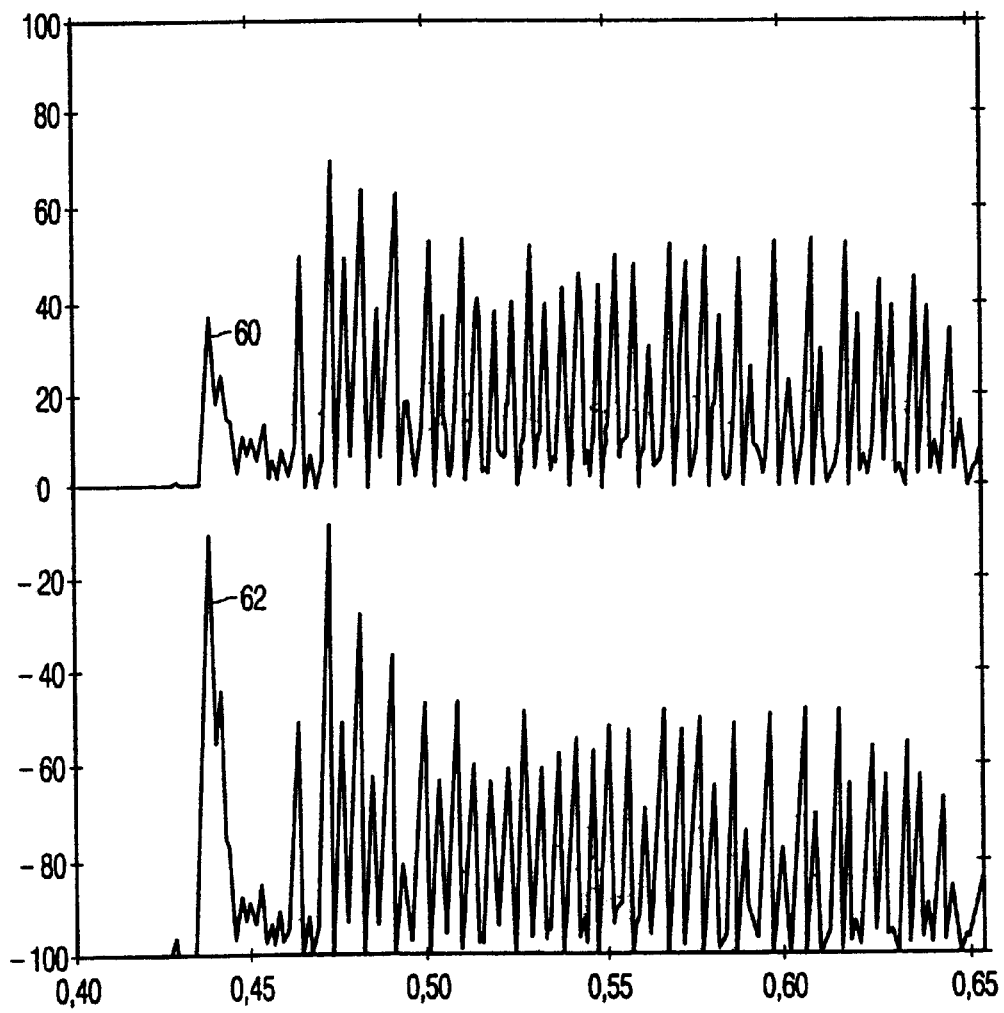

The above object and features of the present invention will be more apparent from the following description of the preferred embodiments with reference to the drawings, wherein:

FIG. 1 shows a block diagram of a hearing instrument according to the invention, FIG. 2 shows a block diagram of a circuit for transforming an audio signal into an output signal according to the present invention, FIGS. 3 and 4 show diagrams of signals generated by the circuit according to the present invention.

In the Figures, identical parts are provided with the same reference numbers.

DETAILED DESCRIPTION OF THE INVENTION

FIG. 1 shows a block diagram of a hearing instrument according to the invention. Such a hearing instrument can be used to improve the perception of sounds by a hearing-impaired user. The hearing instrument comprises a microphone 10 for converting a received sound signal into an electric audio signal 11. This audio signal 11 is transformed in a circuit 12 into an electric output signal 13, which is subsequently converted in a converter 14 to a form which is suitable for the user of the hearing instrument. For instance, if the hearing instrument comprises a conventional hearing instrument which is used by a person who has not completely lost the ability to hear sounds the converter 14 may convert the electric output signal 13 into a sound signal. On the other hand, if the hearing instrument comprises a cochlear implant which is used by a substantially deaf person the converter 14 may convert the electric output signal 13 into a signal which can be used to electrically stimulate the auditory nerves in order to obtain some level of sound perception.

In a preferred embodiment of the hearing instrument according to the invention the hearing instrument comprises a cochlear implant. In this cochlear implant the audio signal 11 is processed according to the so called continuous interleaved sampling strategy. According to this strategy, the audio signal 11 is first filtered by a number of different band-pass filters covering the speech frequency range. This number corresponds to the number of electrode channels (an electrode channel is a combination of electrode surfaces) in the cochlea. In this way the tonotopic organisation (place-frequency coding) of the cochlea is simulated. Next, the envelope of the filtered audio signal in each channel is determined, typically by using a rectifier and a low-pass filter. This envelope is compressed and modulated with an electric current pulse train in each channel.

According to several models which describe the peripheral auditory processing of normal hearing the neural activity at the onset of a sound stimulus is much higher than the activity after the onset. The more suddenly the intensity of the stimulus increases, the higher this activity will be. The duration of this so called short term adaptation is in the order of magnitude of 10 ms. It is assumed that the origin of the adaptation effect is at the inner hair-cell/auditory-nerve synapse. Since a cochlear implant bypasses the haircells, no adaptation effect is seen in the nerve fiber's response to electrical stimulation. FIG. 2 shows a block diagram of a circuit for transforming an audio signal into an output signal according to the present invention in which transformation the short term adaptation effect is incorporated. A number of these circuits arranged in parallel may be included in the hearing instrument according to the invention. The audio signal 11 is band-pass filtered in a filter 20 in order to simulate the tonotopic organisation of the cochlea. By means of a rectifier 22, a channel specific amplifier 24 and a low-pass filter 26 a standard envelope is generated. The cut-off frequency of the filter 26 is 400 Hz. Next, this standard envelope is compressed via a non-linear map in a compressor 28. From the audio signal 11 a second envelope is extracted via the rectifier 22, the amplifier 24 and a second low-pass filter 30. The cut-off frequency of this filter 30 is much lower (for example 20 Hz) than the cut-off frequency of the filter 26 so that a smaller ripple and a larger delay is obtained. Next, the second envelope is amplified in an amplifier 32 and compressed in a compressor 34. By subtracting the resulting signal from the standard envelope by means of a subtractor 36, a peak signal is generated whenever there is a sudden increase in the intensity of the audio signal. The duration of the peak signal is in the order of magnitude of 10 ms. This peak signal is half wave rectified in a half-wave rectifier 38 so that only the positive values of the peak signal are retained. Finally, the peak signal is multiplied in an amplifier 40 by a factor and added to the standard envelope by means of an adder 42 in order to form an enhanced envelope, which emphasises the onset of the typical intensity increases of speech resulting in an improved speech intelligibility. The value of the amplification factor of the amplifier 40 can be different for each electric stimulation channel and for each patient. Ideally, this value is determined via a subjective evaluation by the implantee during a fitting session.

Sudden decreases in the intensity of the audio signal 11 can be emphasised in the output signal 13 by resetting the output signal 13 during a period of about 10 ms. During this period the nerves are not stimulated.

A switch 44 is used to prevent 'false peaks' in the output signal. These can occur when there is a rapid decay in intensity of the received audio signal after a sudden increase in intensity. The ringing caused by the low-pass filters 26 and 30 can lead to a temporary negative output signal, even if the audio signal remains positive. This effect is more prominent for the filter 30, since it has a larger time constant than the filter 26, resulting in 'false peaks'. The inclusion of these 'false peaks' in the output signal can be prevented by opening the switch 44 when the output of the filter 30 is negative.

Another way to incorporate the above mentioned short term adaptation effect is to increase, during a period of about 10 ms, the frequency of the electric current pulse train which is used to modulate the output signal 13.

FIGS. 3 and 4 show typical examples of signals generated by the circuit shown in FIG. 2. In FIGS. 3 and 4, time (in seconds) is plotted on the horizontal axis, and amplitude (in percentage of the dynamic range) is plotted on the vertical axis. For clarity, curve 62 in FIG. 4 is plotted with an offset of -100. The audio signal 11 is the syllable /ka/, and the band-pass filter 20 has cut-off frequencies of 3444 Hz and 5000 Hz. Curve 52 in FIG. 3 represents the output of the compressor 28, curve 50 represents the output of the compressor 34. The amplification of the amplifier 32 is chosen such that the curve 50 is lying above the curve 52 for the stationary part of the signal. However, at the onset of the speech utterance, the curve 52 is lying above the curve 50. This part is exactly the needed peak. Extraction of this peak is done by subtracting the curve 50 from the curve 52 by means of the subtractor 36. Next, the resulting peak signal is half wave rectified in the half-wave rectifier 38 so that only the positive values of the peak signal are retained. Finally, the peak signal is amplified in the amplifier 40 and added to the standard envelope by means of adder 42 in order to form the enhanced envelope.

Examples of the standard envelope (curve 60) and the enhanced envelope (curve 62) for the syllable /ka/ are shown in FIG. 4.

What is claimed is:

1. A hearing instrument comprising a circuit (12) for transforming an audio signal (11) having an onset portion into an output signal (13) characterized in that the circuit (12) comprises emphasis means for emphasizing in the output signal (13) substantial intensity changes of the audio signal (11);

wherein the emphasis means includes a peak generator for generating from the audio signal a peak signal and including means (42) for including the peak signal in the output signal, said emphasis means emphasizing the output signal (13) when an intensity change rate of the onset portion of the audio signal (11) exceeds a predetermined value.

2. A hearing instrument according to claim 1, characterized in that the emphasis means are embodied so as to emphasize the output signal (13) during a period of about 10 ms.

3. A hearing instrument according to claim 2, characterized in that the circuit further comprises filter means (20) for filtering the audio signal (11), whereby the filter means (20) are coupled to the emphasis means so that substantial intensity changes of the filtered audio signal are emphasised in the output signal (13).

4. A hearing instrument according to claim 3, characterized in that the filter means (20) comprise band pass filters.

5. A hearing instrument according to claim 1, characterized in that the hearing instrument is a cochlear implant.

6. A cochlear implant comprising:
an input receiving an audio signal, said audio signal having an onset during which its intensity increases abruptly for short time intervals; and
a circuit coupled to said input and adapted to transform said audio signal into a corresponding stimulation signal, said circuit including an emphasis circuit adapted to detect said onset and to emphasize said stimulation signal in response to said onset.

7. The cochlear implant of claim 6 wherein said emphasis circuit includes a first envelope detector arranged to generate a standard envelope corresponding to said audio signal, a second envelope detector arranged to detect a peak value of said intensity, said stimulation signal being emphasized in accordance with said standard envelope and said peak value.

8. The cochlear implant of claim 7 wherein said emphasis circuit includes a summer used to add said peak value and said standard envelope.

9. The cochlear implant of claim 7 wherein said first envelope detector includes a first filter having a cutoff frequency and said second envelope detector includes a second filter with a much smaller cutoff frequency then the cutoff frequency of said first filter.

10. The cochlear implant of claim 9 wherein said first filter has a cut off frequency of about 400 Hz and said second filter has a cutoff frequency of about 200 Hz.

11. A cochlear implant system comprising:

an input receiving an audio signal having an onset during which its intensity which increases suddenly during a time period;

a circuit adapted to transform said input signal into a plurality of stimulation signals for a plurality of electrode channels, each channel being assigned a frequency range to simulate the totonic organization of a person's cochlea, said circuit including a plurality of filter circuit adapted to generate one of said electrode channels, each filter circuit including an emphasis circuit adapted to detect said onset and to emphasize the stimulation signal on the corresponding electrode channel in response to said onset.

12. The cochlear implant system of claim 11 wherein each said emphasis circuit includes a first envelope generator having a first low pass filter adapted to generate a standard envelope and a second envelope generator having a second low pass filter with a cutoff frequency much lower than the cutoff frequency of the first low pass filter and generating another envelope, a subtractor that subtracts said another envelope from said standard envelope to generate a peak signal indicative of said sudden intensity increase.

13. The cochlear implant system of claim 12 wherein emphasis circuit further includes an amplifier that amplifies that peak signal and an adder that adds the amplified peak signal to said standard envelope.

14. A cochlear implant system comprising:

an input receiving an audio signal including a speech segment characterized by an onset portion; and a circuit coupled to said input and adapted to transform said audio signal into a corresponding stimulation signal, said circuit including an emphasis circuit adapted to emphasize said stimulation signal only during said onset portion, whereby said audio signal during said onset portion is processed differently by said processing circuit then a portion following said onset portion.

* * * * *